US 9,763,997 B2

(12) United States Patent
Fragale et al.

(10) Patent No.: US 9,763,997 B2
(45) Date of Patent: *Sep. 19, 2017

(54) SPRAY DRYING VANCOMYCIN

(71) Applicant: Hospira, Inc., Lake Forest, IL (US)

(72) Inventors: Cynthia Fragale, Kenosha, WI (US); Daniel Brueck, Highwood, IL (US)

(73) Assignee: Hospira, Inc., Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/703,392

(22) Filed: May 4, 2015

(65) Prior Publication Data

US 2015/0231197 A1 Aug. 20, 2015

Related U.S. Application Data

(63) Continuation of application No. 14/262,952, filed on Apr. 28, 2014, now Pat. No. 9,023,258, which is a continuation of application No. 13/343,297, filed on Jan. 4, 2012, now Pat. No. 8,709,310.

(60) Provisional application No. 61/429,844, filed on Jan. 5, 2011.

(51) Int. Cl.
*A61K 38/14* (2006.01)
*A61K 9/16* (2006.01)
*A61K 9/00* (2006.01)
*A61K 38/12* (2006.01)

(52) U.S. Cl.
CPC ............ *A61K 38/14* (2013.01); *A61K 9/0019* (2013.01); *A61K 9/1617* (2013.01); *A61K 9/1623* (2013.01); *A61K 9/1641* (2013.01); *A61K 9/1682* (2013.01); *A61K 9/1694* (2013.01); *A61K 38/12* (2013.01)

(58) Field of Classification Search
None
See application file for complete search history.

(56) References Cited

U.S. PATENT DOCUMENTS

| | | |
|---|---|---|
| 2,911,036 A | 11/1959 | Lazar et al. |
| 4,540,602 A | 9/1985 | Motoyama et al. |
| 4,831,015 A | 5/1989 | Waite |
| 5,458,135 A | 10/1995 | Patton et al. |
| 5,607,915 A | 3/1997 | Patton et al. |
| 5,756,552 A | 5/1998 | Takeuchi et al. |
| 5,785,049 A | 7/1998 | Smith et al. |
| 5,794,647 A | 8/1998 | Denmark et al. |

(Continued)

FOREIGN PATENT DOCUMENTS

| | | |
|---|---|---|
| EP | 03686951 | 12/1990 |
| EP | 0438 747 | 7/1991 |

(Continued)

OTHER PUBLICATIONS

Akade, et al., "Influence of Polyethylene Glycol 6000 and Mannitol on the In-vitro Dissolution Properties Nitrofurantoin of by the Dispersion Technique." pharmazie. 41:849-51 (1986).

(Continued)

*Primary Examiner* — Mary F Theisen
(74) *Attorney, Agent, or Firm* — Kristina L. Konstas

(57) ABSTRACT

A method and formulation for preparing spray dried vancomycin. In various embodiment, the formulation includes vancomycin HCl (10-20%) and one or more of the following PEG (0-5%), mannitol (0-5%), ethanol (0-10%), and a citrate buffer. Spray dried vancomycin has favorable reconstitution times and water content.

21 Claims, 3 Drawing Sheets

(56) References Cited

U.S. PATENT DOCUMENTS

| | | | |
|---|---|---|---|
| 5,853,720 | A | 12/1998 | Pflaum et al. |
| 6,001,800 | A | 12/1999 | Mehta et al. |
| 6,051,256 | A | 4/2000 | Platz et al. |
| 6,077,543 | A | 6/2000 | Gordon et al. |
| 6,253,463 | B1 | 7/2001 | Hansen |
| 6,308,434 | B1 | 10/2001 | Chickering et al. |
| 6,372,258 | B1 | 4/2002 | Platz et al. |
| 6,423,344 | B1 | 7/2002 | Platz |
| 6,433,344 | B1 | 8/2002 | Salisbury et al. |
| 6,479,049 | B1 | 11/2002 | Platz et al. |
| 6,518,239 | B1 | 2/2003 | Kuo et al. |
| 6,582,728 | B1 | 6/2003 | Platz et al. |
| 6,592,904 | B2 | 7/2003 | Platz |
| 6,645,528 | B1 | 11/2003 | Straub et al. |
| 6,673,335 | B1 | 1/2004 | Platz et al. |
| 6,730,923 | B1 | 5/2004 | May et al. |
| 6,763,607 | B2 | 7/2004 | Bayerinck et al. |
| 6,797,258 | B2 | 9/2004 | Platz |
| 6,921,527 | B2 | 7/2005 | Platz et al. |
| 6,932,983 | B1 | 8/2005 | Straub et al. |
| 6,973,741 | B2 | 12/2005 | Beyerinck et al. |
| 7,060,285 | B2 | 6/2006 | Muller |
| 7,108,865 | B2 | 9/2006 | Curatolo et al. |
| 7,138,141 | B2 | 11/2006 | Platz et al. |
| 7,147,869 | B2 | 12/2006 | Dietrich et al. |
| 7,148,211 | B2 | 12/2006 | Mazess et al. |
| 7,414,114 | B2 | 8/2008 | Singh et al. |
| 7,482,024 | B2 | 1/2009 | Kuo et al. |
| 7,550,158 | B2 | 6/2009 | Appel et al. |
| 7,700,130 | B2 | 4/2010 | Truong-Le |
| 7,736,672 | B2 | 6/2010 | Ray et al. |
| 7,780,988 | B2 | 8/2010 | Beyerinck et al. |
| 8,026,286 | B2 | 9/2011 | Curatolo et al. |
| 8,039,619 | B2 | 10/2011 | Sundaram et al. |
| 8,125,333 | B2 | 2/2012 | Ressler et al. |
| 2001/0018072 | A1 | 8/2001 | Unger et al. |
| 2002/0011131 | A1 | 1/2002 | Hosokura et al. |
| 2002/0155183 | A1 | 10/2002 | Bathurst et al. |
| 2002/0197212 | A1 | 12/2002 | Osbakken et al. |
| 2003/0045484 | A1 | 3/2003 | Keith et al. |
| 2003/0124191 | A1 | 7/2003 | Besse et al. |
| 2003/0155531 | A1 | 8/2003 | Clark et al. |
| 2005/0026813 | A1 | 2/2005 | Olstein et al. |
| 2005/0250705 | A1 | 11/2005 | Bassarab et al. |
| 2006/0093677 | A1 | 5/2006 | Chickering et al. |
| 2006/0228251 | A1 | 10/2006 | Schneberger et al. |
| 2006/0292081 | A1 | 12/2006 | Morton et al. |
| 2007/0026083 | A1 | 2/2007 | Doney |
| 2007/0087980 | A1 | 4/2007 | Suzuki et al. |
| 2007/0178165 | A1 | 8/2007 | Altreuter et al. |
| 2008/0096831 | A1 | 4/2008 | Sadatrezaei et al. |
| 2008/0181962 | A1 | 7/2008 | Breczko et al. |
| 2008/0188403 | A1 | 8/2008 | Chaudhary |
| 2008/0194820 | A1 | 8/2008 | Sundaram et al. |
| 2008/0199353 | A1 | 8/2008 | Mlodzinski et al. |
| 2008/0213366 | A1 | 9/2008 | Gowan et al. |
| 2009/0098200 | A1 | 4/2009 | Krayz et al. |
| 2009/0221471 | A1 | 9/2009 | Greenwald et al. |
| 2010/0028440 | A1 | 2/2010 | Dobry et al. |
| 2010/0041589 | A2 | 2/2010 | Keith et al. |
| 2010/0049257 | A1 | 2/2010 | Parker |
| 2010/0049322 | A1 | 2/2010 | McKay |
| 2010/0056784 | A1 | 3/2010 | Lopez et al. |
| 2010/0057910 | A1 | 3/2010 | Kaplinger |
| 2010/0116294 | A1 | 5/2010 | Turok et al. |
| 2010/0305054 | A1 | 12/2010 | Bowman et al. |
| 2011/0124551 | A1 | 5/2011 | Palepu et al. |
| 2011/0207658 | A1 | 8/2011 | Kelleher et al. |
| 2011/0251125 | A1 | 10/2011 | Bay et al. |
| 2011/0257197 | A1 | 10/2011 | Xu |
| 2012/0189666 | A1 | 7/2012 | Dhoot et al. |

FOREIGN PATENT DOCUMENTS

| | | |
|---|---|---|
| JP | H 11 5743 | 1/1999 |
| JP | 11-80022 | 3/1999 |
| JP | 11080022 | 3/1999 |
| JP | 4142149 | 8/2008 |
| WO | 0147542 A1 | 5/2001 |
| WO | WO 01/47542 | 7/2001 |
| WO | 2006055950 | 5/2006 |
| WO | 2010082726 | 7/2010 |
| WO | 2010092395 | 8/2010 |
| WO | 2011035108 | 3/2011 |
| WO | 2011062676 | 5/2011 |
| WO | 2011063419 | 5/2011 |

OTHER PUBLICATIONS

Hodoshima, et al., "Protective Effect of Inactive ingredients against Nephrotoxicity of Vancomycin Hydrochloride in Rats," Drug Metab. Pharmacokinet. 19:68-75 (2004).

Kovalcik & Guillory, "The Stability of Cyclophosphamide in Lyophilized Cakes. Part I. Mannitol, Lactose, and Sodium Bicarbonate as Excipients," J Parenter Sci Technol. 42(1): 29-37 (1988).

http://www.thechargepoint.com//containment-technology/split-butterfly-valves.phuse; Containment Technology—Introduction to Split Butterfly Valves, Containment Theory and the ChargePoint Advantage; printed on Oct. 12, 2010.

http://www.nironic.com/harma_systems/phamaceutical_spray_dryer; Pharmaceutical Spray Dryers PSD, cGMP Solvent Based, printed on Oct. 12, 2010.

ChargePoint Technology, ChargePoint® and ChargePoint® Excel (2010).

ChargePoint Techology, Technical Overview, ChargePoint Containment Valves Solutions for Clean Processing (2010).

Chaftari, et al. "Efficacy and safety of daptomycin in the treatment of Gram-positive catheter-related bloodstream infections in cancer patients," Int. J. Antimicrob Agents; 26:182-186 (2010).

Christopher Goss, "Should we stop using intravenous gentamicin in patients with cystic fibrosis?" Thorax; 63:479-480 (2008).

Henrik Schwartzbach, "Achieving aseptic drying with spray drying technologies." Interview, www.pharmtech.com; 1-3 (2011).

Salman, et al. "Azithromycin in patients with cystic fibrosis chronically infected with Pseudomonas aeruginosa: a randomized controlled trial." JAMA 290:1749-1756 (2003).

Hodoshima, et al., "Decreased renal accumulation and toxicity of a new VCM formulation in rats with chronic renal failure." Drug Metab. Pharmacokinet., 22:419-427 (2007).

Namiki, et al., Evaluation of Vancomycin for I.V. Infusion 0.5 g; Journal of New Remedies & Clinics; 51:611-617 (2007). English Language Summary in text.

SPRAY DRYING VANCOMYCIN

CROSS-REFERENCE TO RELATED APPLICATION

This application is a continuation of U.S. application Ser. No. 14/262,952,filed Apr. 28, 2014, which is now U.S. Pat. No. 9,023,258 and which was a continuation of U.S. application Ser. No. 13/343,297, filed Jan. 4, 2012, which is now U.S. Pat. No. 8,709,310 and which claimed the benefit of U.S. Provisional patent application Ser. No. 61/429,844, filed Jan. 5, 2011, all of which are incorporated herein by reference in their entireties.

BACKGROUND

Field of the Application

The application relates generally to spray drying pharmaceuticals, and particularly to a method for preparing spray dried vancomycin.

Description of Related Art

Vancomycin Hydrochloride (HCl) ($C_{66}H_{75}Cl_2N_9O_{24}$·HCl, molecular weight 1485.71) is an injectable antibiotic that is used to fight susceptible bacteria that cause infections in the body. Vancomycin HCl is typically provided in a powdered form to a health care provider. For example, Vancomycin HCl for Injection (Hospira, Inc., Lake Forest, Ill.) is a sterile dry mixture of vancomycin HCl and may contain a suitable stabilizing agent. Vancomycin HCl is generally prepared into its powdered form by lyophilizing (freeze-drying) an aseptically filled solution of vancomycin HCl in water. The lyophilization process can be inefficient and require expensive production equipment and processing steps.

As an alternative to lyophilization, spray drying involves transformation of a formulation from a fluid state into a dried form by spraying the formulation into a hot drying medium. The formulation can be either a solution, suspension, or a paste. The spray dried product is typically in the form of a powder consisting of single particles or agglomerates, depending upon the physical and chemical properties of the formulation and the dryer design and operation. The basic technique includes the following four steps: a) atomization of the formulation solution into a spray; b) spray-gas contact; c) drying of the spray; and d) separation of the dried product from the drying gas. An aseptic spray drying method can be a more efficient and cost effective process of powder generation compared to lyophilization.

Accordingly, the inventors have identified a need in the art for a suitable formulation and process for spray drying vancomycin.

SUMMARY

In accordance with one embodiment of the present invention, the invention is directed to a method for preparing a vancomycin pharmaceutical formulation in powdered form that can be reconstituted and administered by IV infusion. The method includes dissolving a mixture of vancomycin HCl and polyethylene glycol (PEG) in a solution, and spray drying the solution to form a powder. In various embodiments of the invention, the solution also includes mannitol. In one particular embodiment, the solution includes about 10-20% by weight vancomycin HCl, about 2-4% by weight PEG, and about 2-4% by weight mannitol. In yet another embodiment, the solution includes ethanol.

In another embodiment, the method includes spray drying a solution including vancomycin HCl, PEG and a citrate buffer solution to form a powder than can be reconstituted and administered by IV infusion.

In various aspects of the invention, the method can be conducted under pressurized conditions, and the powder can be transferred under positive pressure to a pressurized storage vessel.

BRIEF DESCRIPTION OF THE FIGURES

An exemplary embodiment of the present application is described herein with reference to the figures, in which.

DETAILED DESCRIPTION

Figure 1:
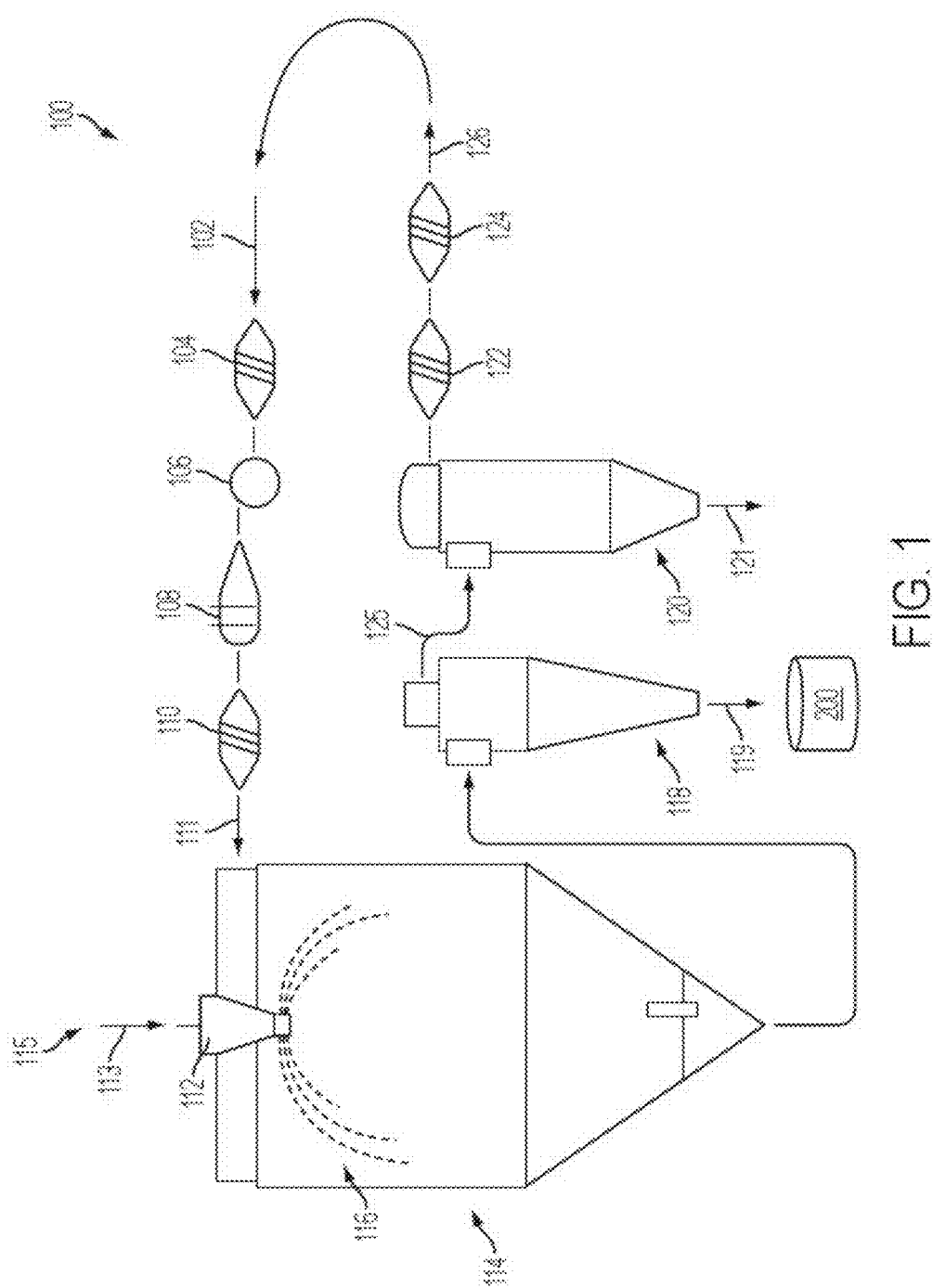
FIG. 1 shows a schematic view of an exemplary spray drying system according to an embodiment of the invention.

The invention provides methods and formulations for providing a spray dried vancomycin product that can be reconstituted and administered by IV infusion. Spray dried pharmaceutical formulations are preferably produced aseptically to avoid the need for further sterilization. The pharmaceutical formulation to be spray dried is preferably selected so as to provide (upon spray drying) a substantially uniform powder with a favorable moisture content and reconstitution profile.

In one embodiment, the invention is directed to a formulation including vancomycin HCl and one or more excipients that are desirable to provide a spray dried formulation suitable for packaging, reconstitution and delivery by IV infusion to a patient. In various embodiments, a vancomycin HCl formulation suitable for spray drying includes vancomycin HCl and polyethylene glycol (PEG) in a polar solvent, such as water for injection (WFI). In one particular embodiment, the formulation includes vancomycin HCl at a concentration of 10-20% by weight, PEG at a concentration of 1-5% by weight, and mannitol at a concentration of 1-5% by weight in water for injection. In another embodiment, the formulation includes vancomycin HCl (10-20% by weight) and PEG (1-5% by weight) in a citrate buffer. In yet another embodiment, the formulation includes vancomycin HCl (10-20% by weight), PEG (1-5% by weight) and ethanol (up to 25% by weight) in water for injection.

Vancomycin HCl API is supplied as a powdered substance with a chromatographic purity of not less than 85%. Polyethylene glycol (PEG) and mannitol are available from a number of known suppliers. The PEG and mannitol used in connection with the present invention are preferably of pharmaceutical quality, parenteral grade, and compliant with US Pharmacopeia, Japanese Pharmacopeia, and/or EP Pharmacopeia standards. The polyethylene glycol used in accordance with the invention preferably has molecular weight of approximately 380-420 Daltons, and is generally referred to as PEG-400.

In another embodiment, the formulation for spray drying vancomycin includes vancomycin HCl at a concentration of about 10% to about 20% (by weight), and more particularly, of about 13% to about 17%. In one embodiment, the formulation for spray drying contains approximately 15% (by weight) vancomycin HCl. The formulation further includes mannitol and PEG-400 at equal or non-equal concentrations of between about 1% to about 5% (by weight), and more particularly between about 2% and about 4% (by weight). In one embodiment, the formulation includes mannitol and PEG-400 in equal concentration of about 3% (by weight) in water for injection (15% vancomycin HCl, 3% PEG-400, 3% mannitol, and 79% water for injection).

In another embodiment, the formulation includes PEG-400 and mannitol in equal concentration of 2.5% (by weight). For this specific embodiment, for clarification, a quantitative composition in solution is provided in Table 1 and a quantitative composition in dried powder is provided in Table 2.

TABLE 1

| Component | Quantity per liter |
|---|---|
| Vancomycin HCl | 150 g |
| PEG-400 | 25 g |
| Mannitol | 25 g |
| HCl | as required to pH 3.4 to 3.6 |
| NaOH | as required to pH 3.4 to 3.6 |
| Water for Injection | as required to 1.00 L |
| Total Volume | 1.00 L |

TABLE 2

| Component | Quantity per gram |
|---|---|
| Vancomycin HCl | 0.75 g |
| PEG-400 | 0.125 g |
| Mannitol | 0.125 g |
| Total Weight | 1.0 g |

In various embodiments of the invention, hydrochloric acid, sodium hydroxide, or other known agents can be used to adjust the pH of the formulation to a pH of about 3.0-3.7, for instance about 3.3-3.6, for example about 3.5.

In various alternative embodiments, the formulation includes vancomycin HCl and PEG-400 in an aqueous citrate buffer (e.g., citric acid/sodium citrate, pH 3.0-3.5). The formulation includes vancomycin HCl at a concentration of about 10% to about 20% (by weight), and more particularly, of about 13% to about 17% (by weight). In one embodiment, the formulation for spray drying contains approximately 15% (by weight) vancomycin HCl. The formulation further includes PEG-400 between about 1% to about 5% (by weight), and more particularly between about 2% to about 4% (by weight). For example, the formulation can include PEG-400 at a concentration of approximately 3% (by weight) or at a concentration of approximately 2.5% (by weight). Upon formulation, the pH of the formulation can be adjusted as necessary to provide the desired pH.

Other suitable excipients for preparing alternative formulations suitable for spray drying vancomycin include glycine (3%-7% (by weight)), sucrose (3%-7% (by weight)), trehelose (1%-4% (by weight)), and poloxamer (0.3%-1% (by weight)).

The process for spray drying vancomycin is preferably undertaken aseptically. Prior to the spray drying step, a vancomycin solution compounding system may be used to rapidly mix the active pharmaceutical ingredient (API), i.e., vancomycin HCl, and excipients in an environmentally controlled system. The system can be a conventional tank and mixer blending system and should minimize operator exposure to the API, and minimize the API's exposure to air/oxygen during the handling, mixing and holding of ingredients prior to spray drying in order to avoid premature vancomycin degradation. The compounded solution undergoes a sterile filtration process prior to the aseptic spray drying process. Following the spray drying process, the resulting powder is harvested into sterile vessels. At the appropriate time, dried powder is then transferred to a filler that fills the resulting spray dried vancomycin in pharmaceutical vials, which are then capped and sealed.

The process may utilize pre-cooled, nitrogen-purged WFI that is added to a nitrogen purged tank through a flow meter to measure the quantity of water. Since the process may be weight based, the full quantity of water, which will be based on the weight of the API to be mixed, can be charged initially.

Once compounding activities have been completed and the mixed solution has met the pre-defined chemistry limits (e.g., pH), the solution is sterile filtered and transferred to the spray dryer. The actual spray drying involves the atomization of a liquid solution (feedstock) into a spray of droplets, and contacting the droplets with hot gas in a drying chamber. The droplets can be produced by, for example, nozzle atomizers. Evaporation of moisture from the produced droplets and formation of dry particles proceed under controlled temperature and gas flow conditions. When the droplets are small enough and the chamber large enough, the droplets dry before they reach the wall of the chamber. The resulting product is collected as a free-flowing material. Powder is discharged continuously from the drying chamber. Operating conditions and spray dryer design are selected according to the drying characteristics of the product and powder specification.

Spray dryers generally include a feedstock pump, an atomizer, a gas heater, a gas disperser, a drying chamber, and systems for exhaust gas cleaning and powder recovery. Referring to FIG. 1, an example spray drying system 100 includes drying gas 102 introduced into a pre-filter 104. In one aspect, the drying gas is nitrogen, and avoids the presence of oxygen. In one embodiment, the drying gas comprises nitrogen with less than 1% oxygen. The drying gas 102 then passes through a fan 106 and a heater 108, which may be an electric heater. The drying gas 102 then passes through a sterilizing gas filter 110 and an inlet gas temperature gauge 111 monitors the inlet gas temperature before it is introduced into a drying chamber 114 via a ceiling gas dispenser. Redundant filtration may be employed to ensure product quality.

The formulation, from the tank and mixer blending system 115, undergoes a sterile filtration process 113 prior to being fed into the drying chamber 114 and atomized by an atomizer 112. The atomizer 112 may be any type of known atomizer that allows for aseptic processing such as a pressure nozzle or a two-fluid nozzle (e.g., available from GEA Process Engineering Inc., Columbia, Md., formerly known as Niro Inc.). The atomizer 112 disperses the liquid formulation into a controlled drop size spray 116. In one particular embodiment, the atomizer is operated with a nozzle protection of 80 kg/hour nitrogen gas at 80° C. The spray 116 is then heated in the drying chamber 114. The heated drying gas evaporates the liquid from the spray and forms dry particles.

After the solution has been atomized and heated, the dry particles exit the drying chamber 116 and proceed into a cyclone 118, which separates the powder from the gas. The powder flows out of the cyclone 118 at outlet 119 into a sterile powder collection vessel 200 and the rest of the gas flows out past an outlet gas temperature gauge 125 toward a cartridge filtration system 120. The cartridge filtration system 120 removes fine particles at outlet 121. The remaining dried gas then flows through a second filter 122 (e.g. a sterile filter), and in some embodiments through a third filter 124, and then back into the drying gas supply at 102. In one embodiment, a vortex eliminator may be used near the bottom of the cyclone 118 to eliminate hot gas from passing through the outlet 119.

As shown in FIG. 1, the dried powder from outlet 119 is collected in a sterile powder collection vessel 200. The collection vessel 200 can be, for example, a 316L grade stainless steel pressure rated vessel, and may be steam sterilized prior to use. The collection vessel 200 may be automatically cleaned, sterilized, and charged with a positive pressure of sterile filtered nitrogen gas.

In an embodiment of the invention shown in FIG. 1, the collection vessel 200 includes a valve assembly, which may be a split butterfly valve or a containment valve, that allows for the sterile transfer of the powder from the cyclone 118 of the spray dryer 100 to the collection vessel 200, and then from the collection vessel 200 to an aseptic powder filler (not shown). The valve assembly is located, for example, between the collection vessel 200 and a bottom of the cyclone 118.

As shown schematically as an exemplary embodiment in FIG. 2a-2e, the valve assembly has an active portion 302 secured to the collection vessel 200 and a passive portion 304 secured to the cyclone 118 of the spray dryer 100. The valve assembly further includes a safety interlock system (not shown) which prevents the active portion 302 from being separated from the passive portion 304 while the valve assembly is open. In one particular embodiment, the valve is a CHARGEPOINT® Excel valve (ChargePoint Technology, Bayville, N.J.).

Figure 2:
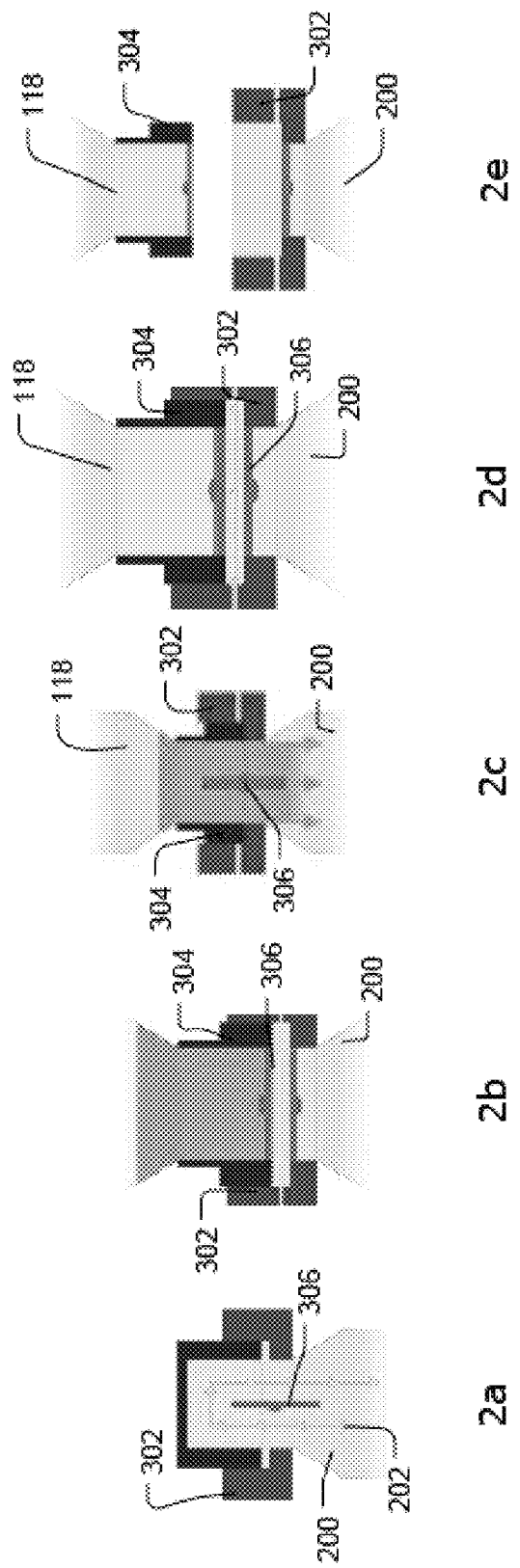
FIGS. 2a-e show a schematic view of a valve for use in a method according to the invention.

In an exemplary use, the collection vessel 200 is placed on a small lift mechanism that centers the collection vessel 200 below the spray dryer cyclone 118 for docking During docking, the active portion 302 of the valve assembly is be sterilized in place (SIP) with vaporized hydrogen peroxide (VHP) 202, as shown in FIG. 2a. Next, as shown in FIG. 2b, the passive portion 304 is connected to the active portion 302 and is purged with VHP to decontaminate previously exposed faces of the active and passive portions 302, 304. The valve assembly includes a valve disc 306 that opens to allow transfer of product, or powder, from the spray dryer cyclone 118 into the collection vessel 200, as shown in FIG. 2c.

When the powder transfer is complete, the valve closes and the feedstock is switched from vancomycin HCl formulation to WFI. In an exemplary embodiment using the CHARGEPOINT® Excel valve, the valve is closed and a control system signals the valve actuator to unlock the two sections of the split butterfly valve, as shown in FIG. 2d, thereby allowing collection vessel 200 to be separated from the passive portion 304, as shown in FIG. 2e. An operator may lower the collection vessel 200 via a local control panel and manually place a pressure cap (not shown) on the collection vessel 200 and lock the pressure cap into position. After the pressure cap is in place, the operator may induce the control system via the local control panel to take a pressure reading from the collection vessel and record all salient vessel characteristics (i.e., vessel I.D. number, date, time, and collection vessel pressure). When complete, the collection vessel may be stored for later use at a powder filler.

In one embodiment, the spray dryer operates at several times the normal operating pressure of conventional spray dryers, including those considered "pharmaceutical grade". In particular, the invention operates at about 1.5-7.0 psig (pounds/square inch gauge), more particularly about 5.5 psig. This higher pressure is required so that the powder transfer vessel is at this higher pressure when powder transfer is complete and the split butterfly valve is closed. This higher pressure allows for pressure reduction as the vessel and vancomycin HCl powder cools to room temperature while maintaining a positive pressure inside the powder transfer vessel. Under positive nitrogen pressure of greater than 1.5 psig, the process and resultant powder will remain sterile in the collection vessel with the positive pressure providing a tamper-evident seal for an extended period, e.g., 14-28 days.

In various embodiments, the spray dryer may utilize a drying gas having an inlet temperature of about 150° C.-250° C., and preferably of about 170° C.-230° C. The drying gas may have an outlet temperature of about 70° C.-150° C., and preferably of about 80° C.-120° C. The nitrogen gas flow rate can range from 650-750 kg/hour, but other flow rates can be used to accommodate the rate of the feedstock and temperature variations.

Collection vessel 200 may then be transferred to an aseptic powder filler and used as a direct transfer vessel for the sterile powder to the filler system. A second valve, such as a CHARGEPOINT® Excel valve as described above, may be used to transfer the sterile powder to the filler system. The powder may then be transferred to dosage vials. After filling, stoppering, and crimping the vials, the vials may be inspected, labeled, and boxed for storage until final release is attained.

The sterility of the spray drying system may be maintained using a variety of methods. The system may include filter elements, e.g., removable filter elements, and the system can be cleaned using a fully automated clean in place (CIP) process. After the CIP process is completed, the filter elements can be installed and may also be integrity tested. Upon acceptable filter integrity testing, the system can be steam sterilized using a fully automated steam in place (SIP) process. When steam sterilization is complete, the spray dryer can be purged with sterile filtered nitrogen gas to remove residual steam and to maintain a positive internal pressure.

Pressure within the system can be maintained using sterile filtered nitrogen gas until the spray drying process is complete.

Two mixing systems may be provided so that one system can be used to feed the spray dryer for approximately 18 hours while the second system is cleaned in place, sterilized in place, and used to mix solution that may be spray dried in the following 18 hour period.

Figure 3:
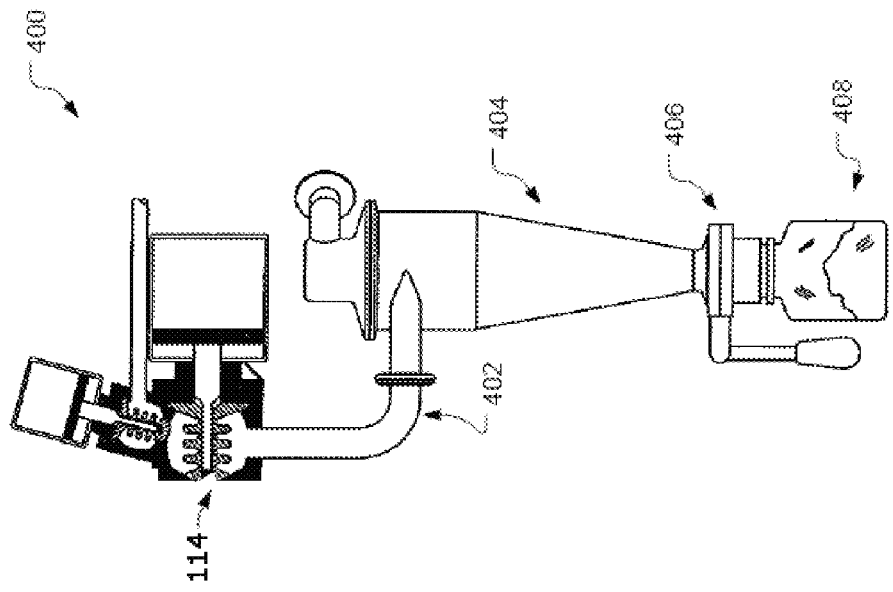
FIG. 3 is a schematic diagram of a powder sampling system for use in a method according to the invention.

In a further embodiment, the spray drying system of the invention includes a powder sampling system 400, shown in FIG. 3, which takes advantage of the high operating pressure of the system as the motive force to discharge powder from a spray dryer product chute 402, which may be used to convey product from the base of the cyclone of the spray dryer to the collection vessel. A valve 406 allows for the sterile transfer of powder from the drying chamber 114 to a receptacle 408 mounted at the discharge of a lab-type sampler cyclone 404 in communication with the spray dryer product chute 402. Transfer of product from the spray dryer product chute 402 to the sampler cyclone 404 is sterile and the critical integrity of the system is not compromised.

The spray dried vancomycin HCl of the present application has advantages over lyophilized vancomycin HCl. For example, the spray drying process of the present application can be used to produce powder more quickly than a standard lyophilization process, with a significant reduction in processing times and operator manipulations/interventions.

In addition, the spray dried vancomycin formulation allows for reconstitution times at least as fast as the lyophilized formulations. For instance, the spray dried formulation can have a reconstitution time of less than 1 minute, for instance, less the 50 seconds, less than 40 seconds, and even less than 30 seconds. The formulation is suitable for delivery by IV infusion to a patient.

EXAMPLES

Example 1

Five batches containing vancomycin HCl (15% by weight), PEG-400 (3% by weight), and mannitol (3% by weight) in WFI were made and then spray dried according the above method. Resultant spray dried powders were tested as shown in Table 3.

TABLE 3

| Batch # | Batch Size | % Moisture* | Reconstitution Time (seconds) | Vancomycin B/Single Largest Impurity (%) |
|---|---|---|---|---|
| 1 | 1 L | 1.7 (GC) | 30 | Not Tested |
| 2 | 5 L | 0.79/0.82 (KF) | 30 | Not Tested |
| 3 | 2 L | 0.77/0.74 (KF) | 23 | 92.5/1.7 |
| 4 | 1 L | 1.0/0.9/1.1 (KF) | 25/27/27/26 | 94.5/1.3 |
| 5 | 10 L | 0.8/0.9/0.8/0.9(KF) | 31/36/31/32 | 93.9/1.3 |

*GC = Gas chromatography;
KF = Karl Fisher

Example 2

Vancomycin HCl, PEG-400, and mannitol were dissolved at various concentrations in ethanol and WFI. The various formulations were spray dried as described above. Resultant powders were tested as shown in Table 4.

TABLE 4

| Batch # | Formulations Vancomycin/PEG-400/Mannitol/Ethanol/WFI | % Moisture (KF) | Reconstitution Time (seconds) | Vancomycin B/Single Largest Impurity (%) |
|---|---|---|---|---|
| 6 | 15%/3%/3%/10%/69% | 0.8 | 45.4 | 94.2/1.5 |
| 7 | 18%/3%/3%/10%/66% | 1.2 | 47.5 | 94.5/1.5 |
| 8 | 15%/2%/5%/0%/78% | 0.7 | 22.9 | 94.6/1.5 |
| 9 | 20%/3%/3%/15%/59% | 0.7 | 61.6 | 94.6/1.6 |

Example 3

Spray drying of various formulations of vancomycin HCl was performed using different parameters for the spray drying process, such as gas temperature, nozzle specifications, and utilizing production scale spray drying equipment. The results of the experiments are shown below in Tables 5 and 6.

TABLE 5

| | Test No. | | | | |
|---|---|---|---|---|---|
| | Test 1 | Test 2 | Test 3 | Test 4 | Test 5 |
| Duration, start-stop | 10:00-10:57 | 11:30-12:05 | 13:49-14:47 | 15:27-15:53 | 10:07-10:52 |
| Drying gas (Nitrogen) | | | | | |
| Main Process gas, kg/hr | 1250 | 1250 | 1250 | 1250 | 1250 |
| Inlet Temperature, ° C. | 180 | 180 | 180 | 210 | 215 |
| Outlet Temperature, ° C. | 111 | 97-100 | 88-90 | 100 | 102-103 |
| Atomizer | | | | | |
| Specification | Pressure Nozzle | | | | |
| Nozzle pressure, bar (g) | 22-26 | 43-47 | 37-42 | 48-53 | 24-25 |
| Nozzle air temp., ° C. | 60 | 60 | 60 | 60 | 60 |
| Nozzle protection gas rate, kg/hr | 95 | 95 | 95 | 95 | 95 |
| Nozzle combination | 67/20 | 67/20 | 67/17 | 67/17 | 57/17 |
| Feed (Vancomycin (15%)/PEG-400 (3%)/mannitol (3%) WFI (79%)) | | | | | |
| Density, g/mL | 1.05 | 1.05 | 1.05 | 1.05 | 1.05 |
| Feed rate, kg/hr | 28-29 | 43-44 | 53 | 60-61 | 60 |
| Powder Analysis | | | | | |
| Residual moisture % (Karl Fischer) | 1.14/1.24 | 1.22/1.31 | 2.35/2.62/2.37 | 1.93/1.85 | 1.44/1.60 |
| Reconstitution time (seconds) | 20 | 21 | 15 | 21 | 26 |
| Particle size, D50, µm | 32 | 33 | 36 | 32 | 43 |

TABLE 5-continued

|  | Test 1 | Test 2 | Test 3 | Test 4 | Test 5 |
|---|---|---|---|---|---|
| Yield | | | | | |
| Collected product, cyclone, kg | 4.5 | 4.6 | 8.9 | 4.9 | 8.1 |
| Collected product, bag filter, kg | | | 0.3 | | |

TABLE 6

|  | Test 6-1 | Test 6-2 | Test 6-3 | Test 6-4 |
|---|---|---|---|---|
| Duration, start:stop | 11:14-12:11 | 12:11-13:15 | 13:15-14:15 | 14:15-15:08 |
| Drying gas (Nitrogen) | | | | |
| Main Process gas, kg/hr | 1250 | 1250 | 1250 | 1250 |
| Inlet Temperature, °C. | 215 | 215 | 215 | 215 |
| Outlet Temperature, °C. | 102-104 | 102-104 | 102-104 | 102-104 |
| Atomizer | | | | |
| Specification | | Pressure Nozzle | | |
| Nozzle pressure, bar (g) | 24-25 | 24-25 | 24-25 | 24-25 |
| Nozzle air temp., °C. | 60 | 60 | 60 | 60 |
| Nozzle protection gas rate, kg/hr | 95 | 95 | 95 | 95 |
| Nozzle combination | 57/17 | 57/17 | 57/17 | 57/17 |
| Feed (Vancomycin (15%)/PEG-400 (3%)/mannitol (3%), WFI (79%)) | | | | |
| Density, g/mL | 1.05 | 1.05 | 1.05 | 1.05 |
| Feed rate, kg/hr | 60 | 60 | 60 | 60 |
| Powder Analysis | | | | |
| Sample time | 12:11 | 13:15 | 14:15 | 15:08 |
| Sample point | Cyclone | Cyclone | Cyclone | Cyclone |
| Residual moisture % (Karl Fischer) | 1.81/1.81 | 1.80/1.87 | 1.60/1.72 | 1.69/1.56 |
| Reconstitution time (seconds) | 20 | 23 | 18 | 21 |
| Particle size, D50, μm | 44 | 44 | 47 | 42 |
| Yield | | | | |
| Collected product, cyclone, kg | 10.3 | 11.8 | 11.2 | 9.3 |
| Collected product, bag filter, kg | | | 0.3 | |

Example 4

Batches for stability testing were made using the spray dried formulation of vancomycin HCl (15% by weight), PEG-400 (3% by weight), mannitol (3% by weight) in WFI, with the API sourced from Abbott Laboratories (North Chicago, Ill.). Spray dried batches were stored at 25° C./60% Relative Humidity (RH), 30° C./60% RH, and 40° C./75% RH for three months. The stability data on moisture by Karl Fischer, pH (of the reconstituted solution), reconstitution time and chromatographic purity are presented in Table 7. The chromatographic purity was examined using the analytical HPLC method described in the current USP (United States Pharmacopeia) monograph for vancomycin. The test results for the API lot used to make the spray dried product were also listed for comparison.

The chromatographic purity of vancomycin B for all samples tested in this study were within USP specifications. All samples were stored at the accelerated conditions of 40° C./75% RH for 3 months and met USP criterion for vancomycin B by chromatographic purity (NLT 80% vancomycin B).

TABLE 7

| Sample Stability Temperature | Stability Temp/Time | % Vancomycin B | Reconstitution Time(s) in Min:Sec | % Moisture | pH |
|---|---|---|---|---|---|
| API Lot 09097619 | Initial | 91.9 | Not performed | Not performed | Not performed |
| Lot 10-0212 | Initial | 91.7 | 0:59 | 0.9 | 3.3 |
| Lot 10-0212 | 25° C./1Month | 91.2 | 0:23, 0:23, 0:22 | 1.0 | 3.3 |
| Lot 10-0212 | 30° C./1Month | 91.2 | Not performed | 1.0 | 3.3 |
| Lot 10-0212 | 40° C./1Month | 90.8 | 0:21, 0:21, 0:21 | 1.0 | 3.3 |
| Lot 10-0212 | 25° C./2Month | 90.6 | 0:21, 0:20, 0:20 | 1.1, 1.2 | 3.4 |
| Lot 10-0212 | 30° C./2Month | 90.2 | 0:30, 0:18, 0:16 | 1.1, 1.2 | 3.3 |
| Lot 10-0212 | 40° C./2Month | 89.2 | 0:17, 0:20, 0:16 | 1.1, 1.2 | 3.4 |

TABLE 7-continued

| Sample Stability Temperature | Stability Temp/Time | % Vancomycin B | Reconstitution Time(s) in Min:Sec | % Moisture | pH |
|---|---|---|---|---|---|
| Lot 10-0212 | 25° C./3Month | 90.8 | 0:20 | 1.1 | 3.3 |
| Lot 10-0212 | 30° C./3Month | 90.6 | 0:21 | 1.1 | 3.4 |
| Lot 10-0212 | 40° C./3Month | 89.4 | 0:17 | 1.1 | 3.4 |

Example 5

Three vancomycin formulations were prepared in WFI or citrate buffer. The solutions were spray dried as described above. Resultant powders were tested along with the vancomycin HCl API for impurities, reconstitution time, and moisture as shown in Table 8.

TABLE 8

| | API | Spray Dry Formulation 1 API 15%, WFI | Spray Dry Formulation 2 API 15%, PEG-400 2.5%, Mannitol 2.5%, WFI | Spray Dry Formulation 3 API 15%, PEG-400 3.0%, citrate buffer |
|---|---|---|---|---|
| Vancomycin B | 94.9% | 92.7% | 94.4% | 94.3% |
| N-Demethyl-vancomycin | 0.6% | 0.7% | 0.6% | 0.6% |
| Other | 4.5% | 6.6% | 5.0% | 5.1% |
| Reconstitution Time (seconds) | N/A | 21, 27, 28 | 25, 26, 31 | 69, 47, 40 |
| Moisture % n = 2 | Not tested | 2.1 | 1.5 | 1.3 |

Although various specific embodiments of the present invention have been described herein, it is to be understood that the invention is not limited to those precise embodiments and that various changes or modifications can be affected therein by one skilled in the art without departing from the scope and spirit of the invention.

The invention claimed is:

1. A method for preparing a powdered vancomycin pharmaceutical product, the method comprising:
   providing a solution comprising vancomycin HCl, mannitol and polyethylene glycol (PEG);
   wherein the ratio, by weight, of vancomycin to PEG is from about 10:1 to about 2.5:1, and
   spray drying the solution to form a powder that can be reconstituted and administered by IV infusion.

2. The method of claim 1, wherein the ratio, by weight, of PEG to mannitol is from about 2:1 to about 1:2.

3. The method of claim 1, wherein the ratio, by weight, of vancomycin to mannitol is from about 10:1 to about 2.5:1.

4. The method of claim 1, wherein the pharmaceutical product has a chromatographic purity for vancomycin B of at least about 89%.

5. The method of claim 1, wherein the pharmaceutical product has a chromatographic purity for vancomycin B of at least about 89% for at least two months after spray drying.

6. The method of claim 1, wherein the pharmaceutical product comprises less than 2.0% water by weight.

7. The method of claim 1, wherein the pharmaceutical product has a reconstitution time of less than about 30 seconds.

8. A method for reducing the loss of vancomycin in a spray-drying process, the method comprising:
   combining vancomycin, mannitol and polyethylene glycol (PEG) in an aqueous solution, wherein the ratio, by weight, of vancomycin to PEG is from about 10:1 to about 2.5:1, and
   spray drying the solution to form a powder.

9. The method of claim 8, wherein the ratio, by weight, of PEG to mannitol is from about 9:1 to about 1:2.

10. The method of claim 8, wherein the ratio, by weight, of vancomycin to mannitol is from about 10:1 to about 2.5:1.

11. The method of claim 8, wherein the pharmaceutical product has a chromatographic purity for vancomycin B of at least about 89%.

12. The method of claim 8, wherein the pharmaceutical product has a chromatographic purity for vancomycin B of at least about 89% for at least two months after spray drying.

13. The method of claim 8, wherein the formulation comprises less than 2.0% water by weight.

14. A method for preparing a powdered vancomycin pharmaceutical product, the method comprising:
   providing a solution comprising vancomycin HCl, polyethylene glycol (PEG), and a citrate buffer, wherein the ratio, by weight, of vancomycin to PEG is from about 10:1 to about 2.5:1, and
   spray drying the solution to form a powder that can be reconstituted and administered by IV infusion.

15. The method of claim 14, wherein the pharmaceutical product has a chromatographic purity for vancomycin B of at least about 94%.

16. The method of claim 14, wherein the pharmaceutical product comprises less than 2.0% water by weight.

17. A powdered vancomycin pharmaceutical product produced by spray-drying a liquid containing vancomycin, polyethylene glycol, and mannitol, wherein the ratio, by weight, of vancomycin to PEG is from about 10:1 to about 2.5:1, and the ratio, by weight, of PEG to mannitol is from about 2:1 to about 1:2.

18. The pharmaceutical product of claim 17, wherein the ratio, by weight, of vancomycin to mannitol is from about 10:1 to about 2.5:1.

19. The pharmaceutical product of claim 17, having a chromatographic purity for vancomycin B of at least about 89%.

20. The pharmaceutical product of claim 17, comprising less than 2.0% water by weight.

21. The pharmaceutical product of claim 17, having a chromatographic purity for vancomycin B of at least about 89% for at least two months after spray drying.

* * * * *